United States Patent [19]

Rodler

[11] Patent Number: 4,457,751
[45] Date of Patent: Jul. 3, 1984

[54] AUTOMATIC INFUSION PUMP

[76] Inventor: Hans Rodler, Pehamweg 3-5, Graz-Neuhart A-8053, Austria

[21] Appl. No.: 261,550

[22] Filed: May 8, 1981

[30] Foreign Application Priority Data

May 16, 1980 [DE] Fed. Rep. of Germany ........ 3018641

[51] Int. Cl.³ .............................................. A61M 5/00
[52] U.S. Cl. ........................................ 604/66; 604/67
[58] Field of Search ................... 604/50, 65, 66, 67, 604/122, 123, 131, 153

[56] References Cited

U.S. PATENT DOCUMENTS

| 3,655,095 | 4/1972 | Kienita | 604/65 X |
| 3,990,444 | 11/1976 | Vial | 604/67 |
| 4,080,966 | 3/1978 | McNally et al. | 604/66 X |
| 4,111,198 | 9/1978 | Marx et al. | 604/65 |
| 4,180,074 | 12/1979 | Murry et al. | 604/66 X |
| 4,213,455 | 7/1980 | Ellson | 604/66 |
| 4,299,218 | 11/1981 | Knigge et al. | 604/67 |
| 4,300,552 | 11/1981 | Cannon | 604/65 |

Primary Examiner—Edward M. Coven
Attorney, Agent, or Firm—Kurt Kelman

[57] ABSTRACT

An infusion pump for the intravenous or intra-arterial infusion of liquid medicines has an electric drive and electronic control, with means so associated with the digital frequency control of the frequency generator (4) for operating the infusion pump motor that the delivered infusion dosage in changed step-by-step after an adjustable time delay by changing the frequency in dependence on physical parameters taken from the patient, and suddenly rising or falling changes in the physical parameters, which are outside a predetermined norm, cause the device to be switched off and generate an alarm.

6 Claims, 2 Drawing Figures

AUTOMATIC INFUSION PUMP

The present invention relates to an infusion pump for the intravenous or intra-arterial infusion of liquid medicines with an electrically-operated drive and an electronic dosing control.

Electrically-operated infusion pumps with an electronic dosing control are known. In the known pumps, the required dose is preferably pre-selected by means of a graduated scale and is introduced into the patient by means of a hose pump. Another type of electrically-operated infusion pumps works with a piston pump, the velocity of the piston being controlled electronically. Pharmacology has provided medicines with a spontaneous action mechanism. They have short-lived effectiveness and even a slight overdose may cause death under certain circumstances. Furthermore, there are blood pressure controlling agents used particularly during surgery to avoid bleeding during the operation. To adjust the blood pressure to a certain value, the preparation must be introduced into the patient continuously in a predetermined dosage. Since an undue lowering produces a critical situation for the patient, the infusion must be controlled constantly by a physician. Another field of application of such agents is in the case of strokes or after operations when the blood pressure situation is critical in intensive care.

To use the preparation effectively, the dosage and the blood pressure must, therefore, be constantly controlled by a physician. Temperature-reducing agents also require a steady control of the infusion agent. In the known arrangements, it was only possible to pre-select a fixed dosage and to monitor the same by a constant control to ascertain whether the dose corresponds to the requirements.

It is the object of the invention to provide an automatic infusion apparatus which permits medicines with a spontaneous action mechanism to be used without constant control by a physician, which may be safely used even with anesthesized and unconscious patients in an operation and which will not endanger the patient even in case of malfunction and which makes a wrong dosing by the servicing personnel impossible. It is also an object of the invention to find the infusion dosage for a predetermined, pre-selectable physical parameter and to introduce this dose into the patient to maintain this pre-selected physical parameter.

The object is obtained according to the invention in the following manner. A frequency generated by an electronic control arrangement is delivered to the electric infusion pump which is operated by a stepping motor or selsyn motor, the frequency being determined by the physical parameter taken from the patient. For this purpose, the physical parameter is compared with an adjustable desired value. Furthermore, the comparison is negated within an upper and lower value. In addition, the motor frequency is changed to a higher value to obtain a larger infusion dose not immediately after a deviation has been found but only after an adjustable time delay so that the human body has time to react to the preparation. At the same time, this results in ignoring short physical changes which may be produced by movements, artifacts and the like. Furthermore, the increase in the infusion dosage and the motor frequency does not proceed spontaneously but in steps which enable the required dose to be infused slowly because of the time delay. Therefore, the infusion dose rises stepwise to the point where the body produces the coresponding reaction and the physical parameter corresponds to the set desired value. A safety measure to take into account spontaneous reactions of the patient consists in reducing the infusion dose to half its value when the physical parameter is exceeded in the direction of the action mechanism and, in case of further excess over a third limit in the direction of the action mechanism, to stop the infusion pump and to generate an alarm. This assures that, if the reactions of the patient are uncontrolled, which is possible in the case of certain medicines, the infusion dosage is either reduced or is immediately stopped. At the same time, the actual throughput of the infusion dosage is measured and the pump is also stopped when this amount is exceeded and an alarm is generated. This avoids false interpretations of the pump in case of a clogged pump connection. At the same time, the pressure in the infusion hose is also used for the same purpose for the control and safety switch-off. When the pressure falls below a certain value, an alarm is also generated since this means that the infusion connection is no longer tight and the infusion preparation does not reach the patient. A further safety measure consists of monitoring air bubbles by means of an electronic eye. The frequency generator is a controlled digital oscillator which receives suitable control values from a digital circuit so that a continuous and, if desired, exponential increase of the infusion dosage and frequency of the oscillator is obtained.

The physical parameter taken from the patient is compared with the desired value by forming the difference and, as long as there is a difference, the parameter at the output causes the oscillator frequency of the motor frequency control to increase within a time delay, the magnitude of the steps being pre-set. The amount of the throughput also generates a parameter which is compared with the motor frequency and, in case of a deviation, also causes the oscillator to be switched off. Assuming a blood pressure reducing agent is used as infusion medium, the arterial blood pressure of the patient is taken and this parameter is converted into an electrical signal forming a differential value with the desired value. This value causes the oscillator frequency to be connected and to begin oscillating in the lowest step. If the differential value still remains after a predetermined delay time, which may set from the outside, the next step is switched on, etc. until the point has been reached when the differential value between the desired and the actual value is zero. Since the infusion dosage rose slowly, the zero value will be maintained for a longer period of time. If the blood pressure then falls after a certain time below a tolerance limit of, for example, 20%, a negative difference between the desired and actual values appears and causes the oscillator frequency to return to half the value. If the blood pressure falls to a further, third limit, which is also pre-set, the negative difference between the desired and actual values becomes even greater and the oscillator is automatically switched off and the infusion dosage becomes zero. At the time time, an alarm device is actuated. If the value falls only below a first limit, the time delay is switched back only one step. Thus, in this case, a limit representing a hysteresis, is provided in the rising range while three limits are provided in the falling range, the first one representing the hysteresis limit within which the next lower step may be selected with suitable time delays while the apparatus is switched to half value when the second step has been exceeded and is stopped after the third limit has been exceeded, and an alarm is generated.

The time delay and the amplitude hysteresis value furthermore avoid control oscillations. The first two limits of the hysteresis may be formed in the digital stage or in the input amplifier itself. Similarly, the second and third limits downwards may be realized by suitable input differential amplifiers but also in the further digital control. This arrangement has the particular advantage that the patient is not only monitored in intensive care, when a constant monitoring of the blood pressure is required, but also receives a corresponding, life-saving preparation. Critical blood pressure changes after operations or after strokes, may not only lead to brain damage, and thus to paralysis and the like, but also to blindness. During an operation, a safe lowering of the blood pressure will avoid excessive loss of blood and, therefore, will improve the chances of recovery.

Further features according to the invention will be explained in detail in the description of the drawing.

Figure 1:
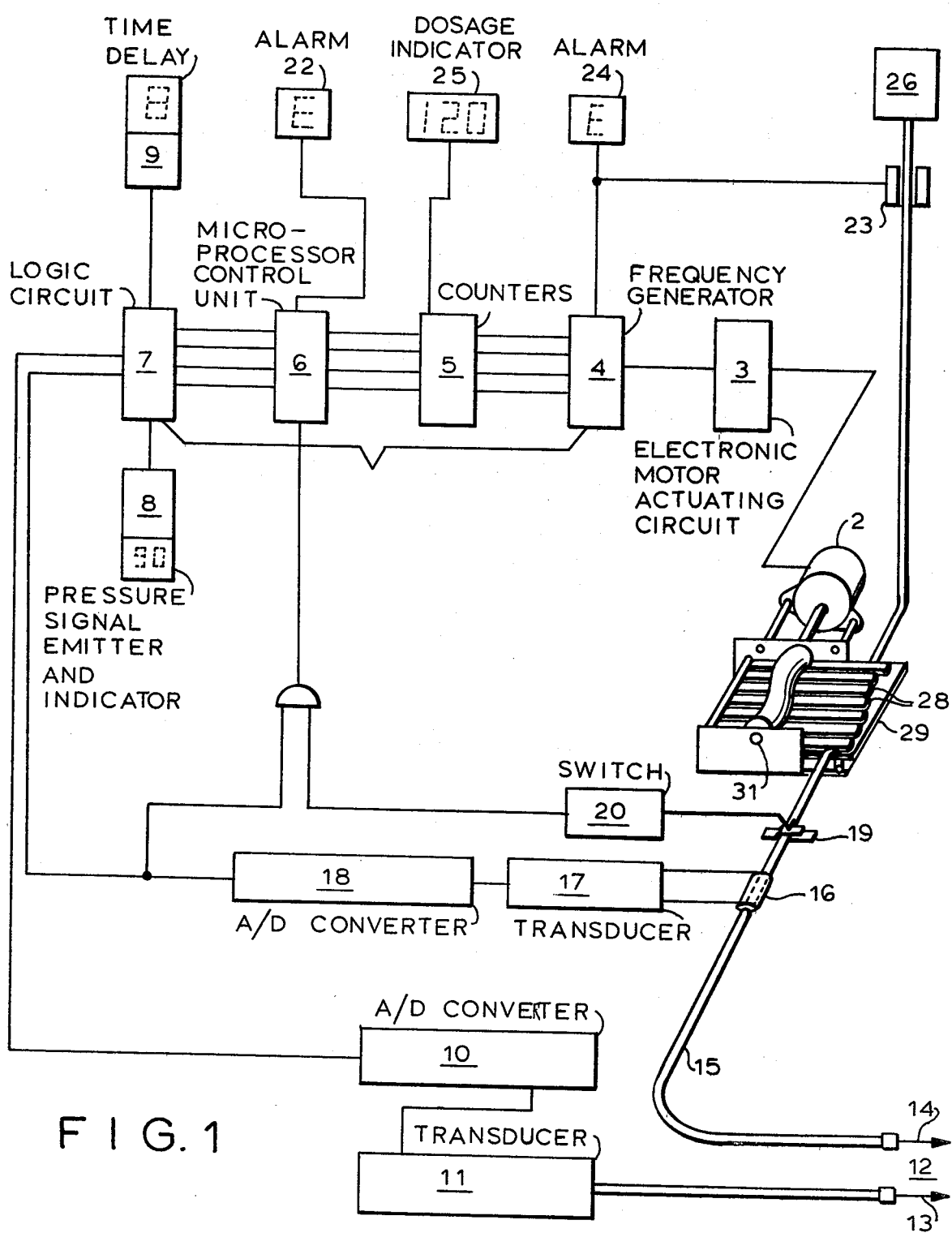
FIG. 1 shows a circuit diagram of an infusion pump.

In FIG. 1, there is shown peristaltic pump 1 which produces a pumping effect in infusion hose 15 by the action of helical spindle 31 pressing bars 28 sequentially against each other, the bars being held by countersupport plate 29. Stepping motor 2 drives the peristaltic pump. This stepping motor is driven by electronic actuating circuit 3 which generates a multi-phase alternating current at the output from a single-phase alternative current at the input. The infusion liquid contained in receptacle 26 reaches the patient through hose 15 along which is arranged a pressure gauge 19 and a dosage measuring device 16, and is injected into the vein of the patient by needle 14. At the same time, needle 13 is used to take the blood pressure from an artery of patient 12 and this is converted by pressure transducer 11 into an electrical signal and is converted into a digital signal by analog/digital converter 10. The dosage measured in device 16 is converted into an electrical signal by dosage transducer 17 and this is converted into a digital signal by analog/digital converter 18. Pressure gauge 19 controls switch 20 which is actuated when the pressure is too low. The signals corresponding to the dosage and pressure parameters are transmitted by AND-getter 21 to control unit 6. This control unit stops pump motor 2 and generates an alarm by indicator 22 when the pressure in gauge 19 is zero and the throughput of liquid is zero or when the throughput of liquid is zero and the pressure is high or when the pressure is zero and the throughput of liquid is high. This function is produced by AND-getter 21. Therefore, logic circuit 6 is not blocked only when pressure gauge 19 shows a certain magnitude and the magnitude of the liquid throughput at measuring device 16 is the correct one.

The digital blood pressure value signal from analog/digital converter 10 and the digital value signal of the dosage from analog/digital converter 18 are delivered to logic circuit 7 which may, for example, be built into an Intel microprocessor 8085 or 8048 or the like. The signal emitter and indicator or the adjustable desired pressure is designated 8 and generates and indicates the comparative value signal for the measured pressure signal for logic circuit 7. The signals corresponding to the lower and upper limit values of the percentage of deviation from the desired value to the actual value are generated in logic 7 into which the signal corresponds to the magnitude of the hysteresis is also programmed. The time delay, which may be set from the outside, is generated at 9, after which the signal is transmitted to module 6 which is constituted by an Intel microprocessor 8085 or 8048. Logic circuit 7 may preferably be constituted by an EPROM or PROM type 8755, for example, or the like or by discrete AND-OR-getters and counters. If the condition is met in logic circuit 7 that the set desired value is lower than the set actual value of the pressure, a signal is transmitted to module 6 after the set time delay has lapsed and module 6 generates the code corresponding to the first frequency stage, assuming that AND-getter 21 permits it, which sets counter module 5 built into microprocessor 8085, 8048 or the like to the first step and simultaneously actuates indicator 25 for the corresponding dosage. Counter module 5 switches on the first frequency of frequency generator 4 which, however, can oscillate in this frequency only when air bubble detector 23, which serves to control the air bubble in infusion hose 15, permits it. In circuit 3, a multi-phase alternating current is generated from a single-phase alternating current for operating the stepping motor. If the desired value is still lower than the measured actual value in logic 7 after a further time delay, this procedure is repeated and counter module 5 is set to the next step and frequency generator 4, which also is built into microprocessor 8085 or 8048, generates the next higher frequency. This is repeated until an equilibrium has been reached between the desired and the actual value within the hysteresis limit. Pump 1, 2 operates at a velocity corresponding to the dosage required by the patient to maintain a certain blood pressure value. If the blood pressure falls below the desired value, counter module 5 and, therefore, frequency generator 4 is set back one step after a time delay at the first hysteresis limit. If the value falls during the time delay to a second percentage limit of 20%, the code value is cut in half in control module 6, whereupon counter module 5 jumps back to half the value prevalent at the time and the pump, therefore, operates at half the rotary speed and delivers half the dosage. If the pressure falls further below a third limit, which lies another 20% below the desired value, control module 6 receives a reset signal from logic circuit 7 and transmits it to counter 5. At the same time, alarm device 22 is actuated, counter 5 returns to zero and oscillator 4 ceases to generate a frequency. Therefore, the pump is stopped instantly. If there is an air bubble detected by electronic eye 23 in hose 15, the oscillator 4 is also stopped but the generated dosage does not return to zero but is maintained at the same magnitude; only the oscillator is switched off and an alarm is generated at 24 while the generated frequency is set at zero and a new procedure begins with the value 1 at stop and alarm and by AND-member 21, i.e. in case of wrong dosages and wrong pressures and a too rapid fall of the actual value. This guarantees maximum safety and also assures that no wrong dosages are delivered to the patient. When the pressure has a large value and the throughput of the liquid is zero, this means that the injection needle is clogged. In other words, the generated dosage does not correspond to the facts. On the other hand, when the throughput is large and the pressure is very small, this means that the injection needle has been pulled out of the vein and the generated dosage again does not correspond to the facts. If the pressure has fallen too rapidly, it means that the patient is not suitable for this preparation. If there is an air bubble in the ducts, the generated dosage is stopped and may, therefore, be maintained at the same magnitude.

Slide registers or individual flip-flops may be used instead of counter modules in circuits 3, 4, 5, 6 and 7, with which the same functions can be obtained, as is known. Circuits 3, 4, 5, 6 and 7 may be constituted according to the invention by a microprocessor, such as 8085 in conjunction with an EPROM 8755 and ROM 8155 or by a plug-in microprocessor 8048 or the like since this essentially has the same structural parts and may be programmed for the same functions.

Figure 2:
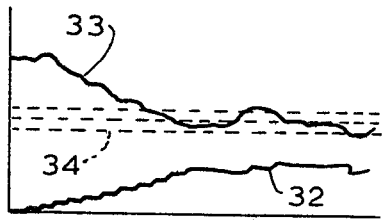
FIG. 2 shows the control curve.

FIG. 2 shows the curves, dosage curve 32 rising slowly step-by-step. This rise may proceed linearly or exponentially or along any other curve by a suitable code formation in control module 6. Blood pressure curve 33 of the patient adjusts itself to the corresponding value which is pre-programmed. The pre-set desired pressure value with the hysteresis limit is shown at 34. The advantages of this arrangement consist in considerably relieving the physician and the personnel, the automatic adaptation of the medicine dosage to the corresponding physical parameter offering additional safety particularly during operations and in intensive care when the patient is unconscious. Particularly after strokes, it is difficult to keep the blood pressure under control and it is particularly important to maintain the blood pressure at a low value in case of a brain hemorrhage so as to avoid further bleeding. But the control of the body temperature is also of great importance, especially during illnesses when the vegitative control fails. Death due to infusion accidents are largely avoided by safely controlling the dosage and pressure.

I claim:

1. An infusion pump for the intravenous or interarterial infusion of a dosage of a liquid medicine into a patient, which comprises
    (a) a drive electrically operated at a controlled frequency for driving the pump, the drive frequency controlling the dosage delivered by the pump,
    (b) means for measuring a physical parameter of the patient and for generating a digital signal corresponding to the measured physical parameter,
    (c) means for generating a reference digital signal corresponding to an adjustable desired parameter,
    (d) an electronic drive control comprised of a microprocessor, the control including
        (1) a frequency generator having an output connected to the drive whereby the frequency of the drive and the corresponding dosage is controlled,
        (2) digital-electronic means in the microprocessor and responsive to the digital signals,
        (3) means for delivering a time delay signal to the digital-electronic means,
        (4) the digital-electronic means in response to the signals maintaining the frequency unchanged as long as the difference between the digital signals is within the limits of a predetermined percentage range of deviation, increasing or decreasing the frequency by a set step after a time delay responsive to the time delay signal when an upper limit of the range of deviation is exceeded or falls below a lower limit, and reducing the frequency to zero when the effect of the medicine changes the measured physical parameter of the patient beyond a predetermined limit of a percentage range within the time delay, and
    (e) digital indicator means connected to the microprocessor for generating an alarm signal when the limits are beyond a normal range.

2. The infusion pump of claim 1, further comprising means for measuring the delivered dosage and for generating a digital signal corresponding to the measured delivered dosage, the digital-electronic means being responsive to the latter digital signal and comparing the same with the frequency for reducing the frequency to zero and generating the alarm signal when the measured delivered dosage is too low in relation to the frequency of the drive.

3. The infusion pump of claim 1, wherein the pump drive is a stepping motor and the pump is a peristaltic hose pump.

4. The infusion pump of claim 3, wherein the physical parameter of the patient is the blood pressure and the liquid medicine is a blood pressure reducing preparation, the drive frequency control increasing the frequency of the pump drive and the corresponding dosage delivered by the pump when the measured blood pressure of the patient increases and decreasing the frequency and the corresponding delivered dosage when the measured blood pressure decreases.

5. The infusion pump of claim 3, further comprising means for measuring the pressure of the liquid medicine in the hose of the pump and for generating a digital signal corresponding to the measured pressure, the digital-electronic means being responsive to the latter digital signal and comparing the same with the reference signal for reducing the frequency to zero and generating the alarm signal when the measured signal deviates from the reference signal.

6. The infusion pump of claim 1, further comprising means for detecting air bubbles in the liquid medicine and generating a corresponding control signal, the digital-electronic means being responsive to the control signal to reduce the frequency of the drive to zero whereby the drive is stopped.

* * * * *